US009664654B2

(12) United States Patent
Fogwill et al.

(10) Patent No.: US 9,664,654 B2
(45) Date of Patent: May 30, 2017

(54) FLAME IONIZATION DETECTION FOR SUPERCRITICAL FLUID CHROMATOGRAPHY EMPLOYING A MATCHED SEPARATION COLUMN AND FLAME BURNER

(71) Applicant: Waters Technologies Corporation, Milford, MA (US)

(72) Inventors: Michael O. Fogwill, South Grafton, MA (US); Joseph D. Michienzi, Plainville, MA (US); James P. Murphy, Franklin, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 14/675,865

(22) Filed: Apr. 1, 2015

(65) Prior Publication Data
US 2015/0301000 A1    Oct. 22, 2015

Related U.S. Application Data

(60) Provisional application No. 61/980,652, filed on Apr. 17, 2014.

(51) Int. Cl.
*G01N 30/68* (2006.01)
(52) U.S. Cl.
CPC .................... *G01N 30/68* (2013.01)
(58) Field of Classification Search
CPC ...................................................... G01N 30/68
See application file for complete search history.

(56) References Cited

U.S. PATENT DOCUMENTS 3,966,411 A * 6/1976 Ross ................. G01N 30/06
436/100
4,845,985 A * 7/1989 Berger ................ G01N 30/28
73/23.25
4,866,270 A * 9/1989 Hall ................ G01N 30/7206
250/282

(Continued)

OTHER PUBLICATIONS

International Search Report for GB Application No. 1506039.5, filed Apr. 9, 2015.

(Continued)

*Primary Examiner* — Paul Hyun
(74) *Attorney, Agent, or Firm* — McCarter & English, LLP; Deborah M. Vernon

(57) ABSTRACT

The present disclosure relates to flame based detection methods for compressed mobile phase chromatography. In particular, the present disclosure relates to the operation of a flame ionization detector for carbon dioxide based chromatography, such as supercritical fluid chromatography. The present disclosure includes a method of matching a chromatographic column with a flame ionization detector inner burner including providing a chromatographic column with an internal diameter, determining an optimal mobile phase flow rate for the chromatographic column, calculating an optimal inner diameter of the inner burner that combined with the internal diameter and flow rate of the column produces optimal detector performance, and providing a flame ionization detector inner burner having an inner diameter substantially equal to the calculated optimal inner diameter.

9 Claims, 3 Drawing Sheets

(56) References Cited

U.S. PATENT DOCUMENTS

| | | | | |
|---|---|---|---|---|
| 5,190,882 A | * | 3/1993 | Schulz | G01N 30/78 210/656 |
| 2005/0178747 A1 | | 8/2005 | Shibamoto | |
| 2006/0213875 A1 | | 9/2006 | Shibamoto | |

OTHER PUBLICATIONS

Thurbide, K. B., et al., "Packed-Column Supercritical Fluid Chromatography with Splitless Flame Ionization Detection," Canadian J. Chem., 2004, vol. 82, 479-482.

Mah, C., et al., "An Improved Interface for Universal Acoustic Flame Detection in Modified Supercritical Fluid Chromatography," J. Sep. Sci., 2008, vol. 31, 1314-1321.

McCabe, R. W., et al., "Kinetics and Reaction Pathways of Methanol Oxidation on Platinum,"J. Phys. Chem., 1986, vol. 90, No. 7, 1428-1435.

Agrell, J., et al., "Production of Hydrogen from Methanol over Cu/ZnO Catalysts promoted by ZrO2 and Al2O3," J. Catalyst, 2003, vol. 219, 389-403.

\* cited by examiner

FLAME IONIZATION DETECTION FOR SUPERCRITICAL FLUID CHROMATOGRAPHY EMPLOYING A MATCHED SEPARATION COLUMN AND FLAME BURNER

CROSS REFERENCE TO RELATED APPLICATIONS

This application claims priority to and the benefit of U.S. Provisional Application No. 61/980,652 filed Apr. 17, 2014, and entitled "Flame Ionization Detection for Supercritical Fluid Chromatography Employing a Matched Separation Column and Flame Burner" which is incorporated herein by reference in its entirety.

TECHNICAL FIELD

The present disclosure relates to flame based detection methods for compressed mobile phase chromatography. In particular, the present disclosure relates to the operation of flame ionization detection (FID) for carbon dioxide based chromatography, such as supercritical fluid chromatography (SFC).

BACKGROUND

Flame ionization detection in supercritical fluid chromatography is traditionally provided by gas chromatography (GC) instrumentation. Such instrumentation is designed to operate at relatively low mobile phase flow rates. Typical mobile phase flow rates for capillary GC columns are 0.5-15 mL/min, and typical flow rates for packed GC columns are 10-60 mL/min. Analytical-scale packed column SFC generates much higher mobile phase flow rates. Upon decompression, SFC mobile phases can generate mobile phase flow rates up to or greater than 2,500 mL/min. In some applications, the flow is split to reduce the flow rate to the detector. Splitting the flow, however, negatively impacts sensitivity and introduces quantitation variability related to variable split flow values. In other applications, the FID burner diameter can be altered to reduce the linear velocity of the decompressed mobile phase flow through the burner in order to maintain a steady flame. See K. B. Thurbide, S. Gilbert. *Canadian Journal of Chemistry* 82 (2004) 479-482.

Chromatographic columns are available in a variety of different internal diameters (i.d.). As a result, chromatographic columns have a wide variety of optimum mobile phase flow rates. To accommodate these various rates in an FID while maintaining a steady flame is difficult because the alteration or adjustment of the burner inner diameter is non-trivial. Detector hardware alterations and lengthy optimizations must be performed every time the separation column geometry is changed in a SFC-FID system to ensure optimal detector sensitivity. To provide nominal, or eventually optimized, detector sensitivity and avoid extinguishing the flame, the burner diameter must be matched to a column flow rate to ensure adequate decompressed mobile phase linear velocity.

SUMMARY OF INVENTION

The present disclosure relates to flame based detection methods for compressed mobile phase chromatography. In particular, it relates to the operation of a flame ionization detector for carbon dioxide based chromatography, such as supercritical fluid chromatography. In one aspect, the present disclosure relates to a method of matching an FID burner having optimized geometry for the optimum mobile phase flow rate of a specific separation column which eliminates the complexities encountered when optimizing a FID after installation of a new column.

In one embodiment, the present disclosure relates to a method of matching a chromatographic column with a FID inner burner, including (i) providing a chromatographic column with an internal diameter; (ii) determining an optimal mobile phase flow rate for the chromatographic column; (iii) calculating an optimal inner diameter of the inner burner that combined with the internal diameter and flow rate of the column produces optimal detector performance; and (iv) providing a FID inner burner having an inner diameter substantially equal to the calculated optimal inner diameter. The method can further include installing the FID inner burner within a fixed FID outer burner of the flame-based detector.

In another embodiment, the present disclosure relates to a method for flame ionization detection in a chromatography system comprising (i) providing a flame ionization detector having a fixed outer burner that accommodates a plurality of inner burners each having a different size that corresponds to a mobile phase flow rate; (ii) disposing the flame ionization detector in fluid communication with a chromatography system having one or more mobile phase flow rates; (iii) selecting a mobile phase flow rate; and (iv) selecting an inner burner in response to the selected mobile phase flow rate.

In another embodiment, the present disclosure relates to a kit including (i) a chromatographic column with an internal diameter; and (ii) a commercially available FID inner burner with an inner diameter, wherein the FID burner inner diameter is matched to the chromatographic column internal diameter to produce optimal detector performance.

In yet another embodiment, the present disclosure relates to a chromatography apparatus comprising (i) a chromatography column capable of separating one or more analytes based on a chemical or physical property; and (ii) a flame ionization detector disposed in fluid communication downstream of the column, wherein the flame ionization detector has a fixed outer burner that accommodates a plurality of inner burners that each have a different size that corresponds to a mobile phase flow rate.

The above embodiments can include one or more of the following features, such as, the FID inner burner can be selected from commercially available FID inner burners having an inner diameter within +/−50% of the calculated optimal inner diameter. The optimal mobile phase flow rate can be the flow rate which has the lowest minimum plate height as determined by the van Deemter Equation for the chromatographic column.

The present disclosure provides a number of advantages over current apparatus and methods. For instance, it addresses the problems of mismatched column and inner burner gas flows involved with adapting an SFC system to a gas chromatography flame-based detector. A matched chromatographic column and FID inner burner can reduce the time needed to optimize the response of the FID. They can also eliminate the complexity encountered when changing column diameters during method development of an SFC system including an FID. The present disclosure is an example of a plug and play combination which may be utilized, for example, in a microfluidic device housing a separation channel, heated variable restrictor and an FID burner.

DETAILED DESCRIPTION

Figure 1A:
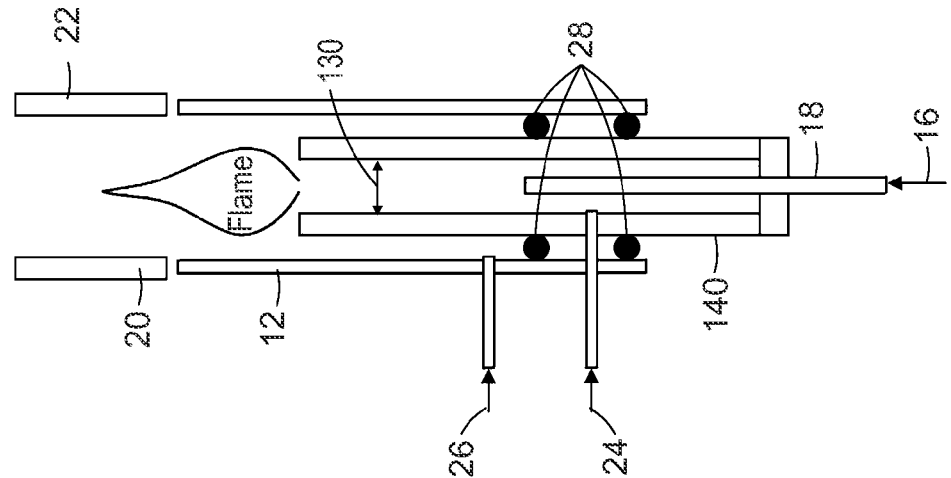
FIGS. 1A and 1B show schematic diagrams of FID designs employing such a replaceable burner. The burner in FIG. 1A can be exchanged with a larger inner diameter (i.d.) burner replacement (FIG. 1B) to allow the use of a larger i.d. column.

The present disclosure relates to flame based detection methods for compressed mobile phase chromatography. In particular, the present disclosure relates to the operation of a flame ionization detector for carbon dioxide based chromatography, such as supercritical fluid chromatography.

In one embodiment, the present disclosure relates to a method of matching a chromatographic column with a FID inner burner, including (i) providing a chromatographic column with an internal diameter; (ii) determining an optimal mobile phase flow rate for the chromatographic column; (iii) calculating an optimal inner diameter of the inner burner that combined with the internal diameter and flow rate of the column produces optimal detector performance, detector sensitivity, or optimal detector response; and (iv) providing a FID inner burner having an inner diameter substantially equal to the calculated optimal inner diameter.

The chromatographic column can be any column known to one skilled in the art used for performing compressed mobile phase separations. For example, the chromatographic column can be a wall coated open tubular column (e.g., microfluidic in nature made in silica, metal, polymer, etc. or in a long spool of fused silica tubing) ranging from 50 to 530 μm i.d. and 1 to 105 m in length; a packed column with 1 to 4.6 mm i.d., 5 to 25 cm in length, packed with 1 to 10+ μm packing media; a packed microscale column (e.g., 85 to 500 μm i.d., 5 to 25 cm in length, packed with 1 to 10+ μm media) either made in a conventional tube (e.g., metal or glass) or in a planar microfluidic device (e.g., silica, metal, polymer, etc).

The compressed mobile phase chromatographic techniques can be any technique known to one skilled in the art including SFC, carbon dioxide based chromatography, GC and solvating GC. For example, the technology of the present disclosure can be adapted to SFC systems operating with preparative, semi-preparative, analytical, or capillary-scale packed-bed columns or open tubular columns. The columns can be prepared in conventional metallic, fused silica, or polymeric tubes or in metallic, ceramic, or polymeric microfluidic platforms.

In some embodiments, the present disclosure is applicable to the combination of a microfluidic device into a stationary FID chassis (i.e., inserting a microfluidic open tubular GC column, a microfluidic packed GC column, or a microfluidic SFC column into the same receptacle of the detector). In other embodiments, the present disclosure relates to a microfluidic device that is merely a transfer line to which a split leg from a larger SFC system is attached. The present disclosure also relates to embodiments wherein the separation column and burner are a part of a single microfluidic device.

The compressed mobile phase can include any compressed mobile phase known to one skilled in the art that are used to perform chromatography including carbon dioxide.

In some embodiments, the mobile phase can contain carbon dioxide, water, argon, nitrogen, helium, hydrogen, various CFCs, fluorocarbons, $SF_6$, $N_2O$ or combinations thereof. In certain embodiments, the mobile phase includes additives or modifiers, such as, for example, methanol can be introduced into the mobile phase.

The inner diameter of the chromatographic column can vary between about 0.05 mm and about 50.0 mm. In particular, the inner diameter can vary between about 0.15 mm and about 5.0 mm. The optimal mobile phase flow rate for the chromatographic column can vary depending on the application, such as it can be a mobile phase flow rate that provides the best separation (e.g., best resolution between one or more critical pairs), the fastest separation (e.g., baseline resolution of compounds of interest in the shortest time), etc. As used herein, the term "optimal" is used to describe the measurement of a variable or term that is within about 50%, or about 40%, or about 30%, or about 20%, or about 10%, or about 5% of the value of the variable or term as measured, calculated or theorized for a particular set of conditions. One method for determining or estimating the optimal mobile phase flow rate is calculating the flow rate which has the lowest minimum plate height as determined by the van Deemter Equation for the chromatographic column and, as applicable, the system conditions.

In some embodiments, it is desirable to operate at a flow rate faster than the minimum plate height as determined by the van Deemter Equation. A small amount of chromatographic efficiency can be sacrificed to achieve a separation in a shorter amount of time. The optimal flow rate can be a multiplier of the flow rate determined as having the minimum plate height via the van Deemter Equation. The multiplier can be 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 times the minimum plate height as determined by the van Deemter Equation. These values can also be used to define a range, such as about 0.9 to about 2.0. In other embodiments, the multiplier can range from about 1.01 times to about 3.0 times faster, or from about 1.5 times to about 3.0 times faster.

In one embodiment, a change in optimal flow due to column diameter change can be estimated by squaring the diameters. For example, $$\text{flow } B = \text{flow } A \times [(\text{col } B)^2/(\text{col } A)^2] \quad \text{(Equation 1)}$$

Thus, increasing from a 1 mm to a 2 mm inner diameter column would result in roughly a 4× increase in flow.

The calculation of an optimal inner diameter of the inner burner can be one that when combined with the internal diameter and flow rate of the column produces optimal detector performance, optimal detector sensitivity, optimal detector response, or any combination thereof. For example, the optimal inner diameter of the FID inner burner can be calculated as substantially equal to the calculated value according to Equation 2:

$$d = \mu/175 \quad \text{(Equation 2)}$$

wherein d is the inner diameter of the FID inner burner in mm, and μ is the decompressed optimal mobile phase flow rate in mL/min.

The inner diameter of the inner burner can vary between about 0.1 mm and about 13.0 mm. In particular, the inner diameter can vary between about 0.5 mm and about 5.0 mm (common for SFC), or about 0.1 mm and about 1.0 mm (common for GC). The inner burner can have an inner diameter substantially equal to the calculated optimal inner diameter. The inner burner can have an inner diameter within about +/−50%, +/−40%, +/−30%, +/−20%, +/−10% or +/−5% of the calculated optimal, or determined, inner diameter. In one embodiment, the inner burner can be a commercially available FID inner burner. The commercially available FID inner burner can have an inner diameter within about +/−40%, +/−30%, +/−20%, +/−10% or +/−5% of the calculated optimal, or determined, inner diameter.

The method of the present disclosure further includes installing the FID inner burner within a fixed FID outer burner of the flame-based detector. The matched chromatographic column and FID inner burner can reduce the time needed to optimize a response of a flame-based detector in a chromatography system. A match chromatographic column and FID inner burner can be a combination of column and inner burner wherein the i.d. of the inner burner is within 50% of the optimal or determined value, as provided herein, to produce optimal detector performance, optimal detector sensitivity, optimal detector response, or any combination thereof.

The present disclosure also relates to a method for flame ionization detection in a chromatography system comprising (i) providing a flame ionization detector having a fixed outer burner that accommodates a plurality of inner burners each having a different size that corresponds to a mobile-phase flow rate; (ii) disposing the flame ionization detector in fluid communication with a chromatography system having one or more mobile phase flow rates; (iii) selecting a mobile-phase flow rate; and (iv) selecting an inner burner in response to the selected mobile-phase flow rate.

The present disclosure also relates to a kit including (i) a chromatographic column with an internal diameter; and (ii) a commercially available FID inner burner with an inner diameter, wherein the FID burner inner diameter is matched to the chromatographic column internal diameter to produce optimal detector performance, optimal detector sensitivity, or optimal detector response.

The present disclosure also relates to a chromatography apparatus comprising (i) a chromatography column capable of separating one or more analytes based on a chemical or physical property; and (ii) a flame ionization detector disposed in fluid communication downstream of the column, wherein the flame ionization detector has a fixed outer burner that accommodates a plurality of inner burners that each have a different size that corresponds to a mobile phase flow rate.

In one embodiment, the present disclosure relates to a method of assisting a researcher or chromatographer in selecting the combination of chromatography column and FID inner burner configuration to use. In some situations, the column diameter dictates the mobile phase flow rate, and the mobile phase flow rate dictates the FID burner size. When a particular column is selected, such as an analytical column having a 3.0 mm i.d., an appropriate sized FID burner is also selected, recommended or provided which is associated with the column. The provision of a matched inner burner to the chromatographic column, or interface to the detector, saves time. The interface can include all necessary hardware including a potential split tee, a restrictor, and the burner.

In some embodiments, known optimization procedures can also be used. For example, the placement of the transfer line inside of the burner can be fixed. The transfer line is the restrictor through which the column effluent travels through. This line can be fixed within the inner, replaceable burner to eliminate this variable when the burner is changed. The placement of this line can affect detector performance. If the restrictor tip is too close to the top of the burner, the mobile phase may not have adequate time to decompress, expand and achieve a stable linear velocity. An appropriate distance from the restrictor tip to the top of the burner is one that provides adequate mixing of the mobile phase and hydrogen combustion gas. The distance from the restrictor tip to the top of the burner can be about 0 mm to about 50 mm. In particular, the fixed distance of the restrictor tip can be about 0, 2, 4, 6, 8, 10, 12, 14, 16, 18, 20, 22, 24, 26, 28, 30, 32, 34, 36, 38, 40, 42, 44, 46, 48 or 50 mm. These values can also be used to define a range, such as between about 20 and 40 mm.

Other factors that can be adjusted when changing the column diameter (e.g., changing the mobile phase flow rate) include adjusting the distance from burner to the collector electrode. For example, larger columns require larger burners. Larger burners can accommodate larger flames which would require a larger space between the burner and the collector. Adequate separation between the top of the burner and the collector is required. If the flame is too large, it will touch the collector and 'short' the detector causing saturation of response. The size of the flame depends on both the mobile phase flow rate and the burner diameter. Based on the values for these parameters, the distance from burner to the collector electrode can be determined. The separation between the top of the burner and the collector is about 1 mm to about 30 mm. In particular, the separation between the top of the burner and the collector can be about 1, 2, 4, 6, 8, 10, 12, 14, 16, 18, 20, 22, 24, 26, 28 or 30 mm. These values can also be used to define a range, such as between about 10 and 20 mm.

Traditionally, gas chromatography is performed using a single burner design which accommodates a wide range of column flow rates. Nitrogen makeup gas is often introduced to the mobile phase stream downstream of the column, as needed. This makeup gas is introduced when the mobile phase flow rate is too low for the burner diameter to provide optimum detector response. Ideally, the makeup gas is added so that the total of the mobile phase flow rate and makeup gas is equal to the highest possible mobile phase flow rate at which the FID burner is optimized.

In some applications, chromatographic techniques using compressed mobile phases do not require makeup gas. Upon decompression, these techniques have mobile phase flow rates 10-100× or more greater than traditional gas chromatography. One method of reducing the mobile phase flow into the FID is to use a split flow adaptor. Using a split, the mobile phase is introduced to the FID at lower flow rates as compared to the main mobile phase flow stream. These lower mobile phase flow rates may be comparable to traditional GC flow rates or be set at a value greater than traditional GC mobile phase flow rates. In other applications, these techniques use makeup gas. In some separations, the addition of nitrogen as makeup gas in a 1:1 ratio can improve response twofold. The use of makeup gas (makeup gas to mobile phase) from a ratio of 0:1 to 1:1 is also contemplated in the present disclosure.

In some embodiments, the split ratio can be controlled, recorded and adjusted during a separation. The mobile phase flow rate can also be measured during a separation. Accordingly, the split can be varied during the run to deliver a pre-determined mobile phase flow rate to the FID to maintain optimal detector performance throughout the separation. The detector response to analytes eluting as a result of being exposed to different split ratio values will have a proportional increase or decrease in their response corresponding to the split ratio. The split ratio can be used to correct or normalize the signal received from the FID detector.

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

FID Design with a Replaceable Burner

In this example, one aspect of the present disclosure is highlighted, namely a chromatography system having an FID with a fixed outer burner that can accommodate a number of different inner burners having different sizes that correspond to different mobile phase flow rates.

Figure 1B:
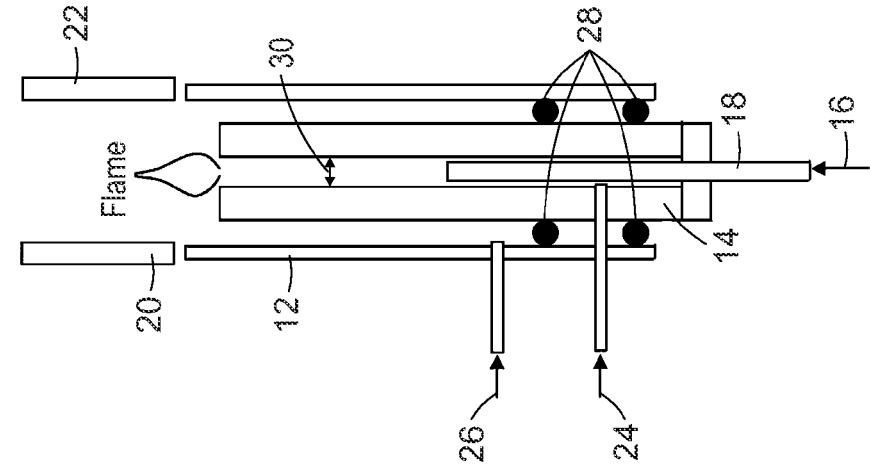

FIGS. 1A and 1B show a schematic of FID designs (10) (100) having a fixed outer burner (12) and employing a replaceable inner burner (14) (140). Under an initial set of conditions (FIG. 1A), a column having a 2.1 mm i.d. is used to generate a column effluent (16). The mobile phase flow rate is about 0.6 mL/min of dense mobile phase which is roughly equivalent to about 300 mL/min of decompressed flow. The column effluent (16) passes through a restrictor (18) as it enters the inner burner (14). The outer burner (12) and burner housing is a piece of 0.500 inch outer diameter (o.d.) by 0.460 inch i.d. stainless steel tubing. The inner burner (14) (replaceable) is a piece of 0.250 inch o.d. by 0.085 inch i.d (30). stainless steel tubing. The FID has combustion gas inlet for both hydrogen (24) and air (26). Vespel ferrules are used as gas seals (28). The signal from the flame is captured using a collector electrode (20) connected to an electrometer (22).

Under a second set of conditions (FIG. 1B), a second column having a 4.6 mm i.d. is used. A second mobile phase flow rate of about 1.5 mL/min is used. The inner burner (14) is easily and quickly replaced with a second stainless steel inner burner (140) having a 0.250 inch o.d. and a 0.188 inch i.d (130). The larger column i.d. results in a larger flow rate and the need for a larger i.d. inner burner to keep the flame and detection conditions optimized.

Figure 2:
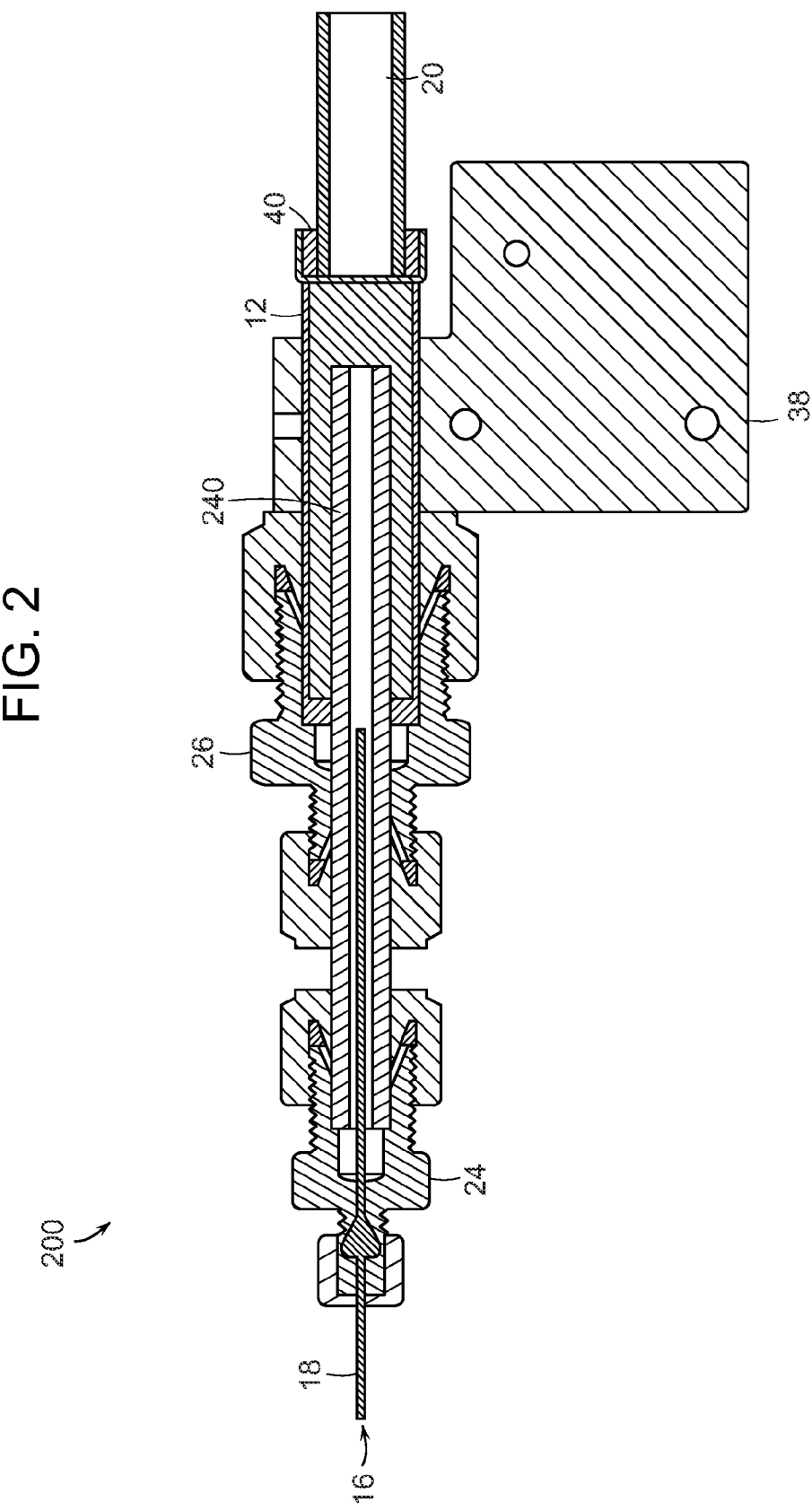
FIG. 2 shows another schematic diagram of a FID design employing such a replaceable burner.

FIG. 2 shows another schematic of a burner design (200). In this design, the gas is routed along with the gas seals which can allow for a quick and easy replacement of an inner burner/column (240) assembly. The gas can be $CO_2$ at a flow rate within 1-3 mL/min, e.g., about 1.5 mL/min. The column effluent (16) passes through a restrictor (18) as it enters the inner burner (240). The burner/restrictor/column device can be inserted into a fixture which provides hydrogen gas. The inner burner (240), here a ¼ inch by 4.5 mm inner burner (removable) can be positioned at the correct distance from collector electrode (20). The collector electrode is protected by a ceramic isolator (40). An outer burner (12), here a ½ inch by 0.460 inch outer burner, can be used. Oxidant (e.g., air) (26) could be provided by the fixture. The FID burner design also includes a heater block (38).

Example 2

Determination of the FID Inner Burner Inner Diameter

In this example, another aspect of the present disclosure is highlighted, namely the determination of an appropriately sized inner burner using the known parameters of the chromatographic system.

For a given chromatography column, the inner diameter of the FID inner burner can be estimated by the following Equation 2:

$$d = t/175 \qquad \text{(Equation 2)}$$

wherein d is the inner diameter of the FID inner burner in mm, and μ is the decompressed optimal mobile phase flow rate in mL/min. Equation 2 was derived from the following experimental data collected. Five (5) burner internal diameters were tested. Two burners having an internal diameter of 0.279 mm i.d. and 0.508 mm i.d. were tested using an Agilent 6890A GC with no column (just a piece of silica tubing to provide restriction). The mobile phase (He) flow rate was increased (and corresponding hydrogen and air flows) until the flame became unstable. The mobile phase flow rate was reduced until the flame was stable. The flow rates in the tables are the maximum flow rates exhibiting stable flames. A 0.965 mm i.d. burner is the burner in a SRI model 110 FID. A split-flow interface in a chromatographic system was used (e.g., 3.0×150 mm, 1.8 μm HSS C18 column at 40° C., 1.5 mL/min of 100% $CO_2$, 2500 PSI BPR pressure). A 0.5 μL injection of hexadecane in carbon disulfide at 2 μg/uL was injected. Experiments were run at 20, 40, 50, 100, and 200 mL/min of decompressed $CO_2$ directed to the FID. The 200 mL/min was the maximum flow rate that could be supported with a stable flame. The 2.159 mm i.d. burner employed a 2.1×150 mm, 5 um C18 column employing full-flow interface to a custom-built FID. It was operated at 0.6 mL/min of dense $CO_2$. The 4.526 mm i.d. burner used a 4.6×150 mm, 5 um C18 column on the same custom system. The column flow rate was 1.5 mL/min. Other conditions for the 2.159 mm i.d. and 4.526 mm i.d. burners were similar to the 0.965 mm i.d. burner. The last two were near the maximum flow rate supported however, no exhaustive experiments were performed to establish the maximum sustainable flow on these two burners.

| Burner ID (mm) | Mobile Phase Flow Rate (mL/min) |
|---|---|
| 0.279 | 20 |
| 0.508 | 44 |
| 0.965 | 200 |
| 2.159 | 330 |
| 4.526 | 825 |

Figure 3:
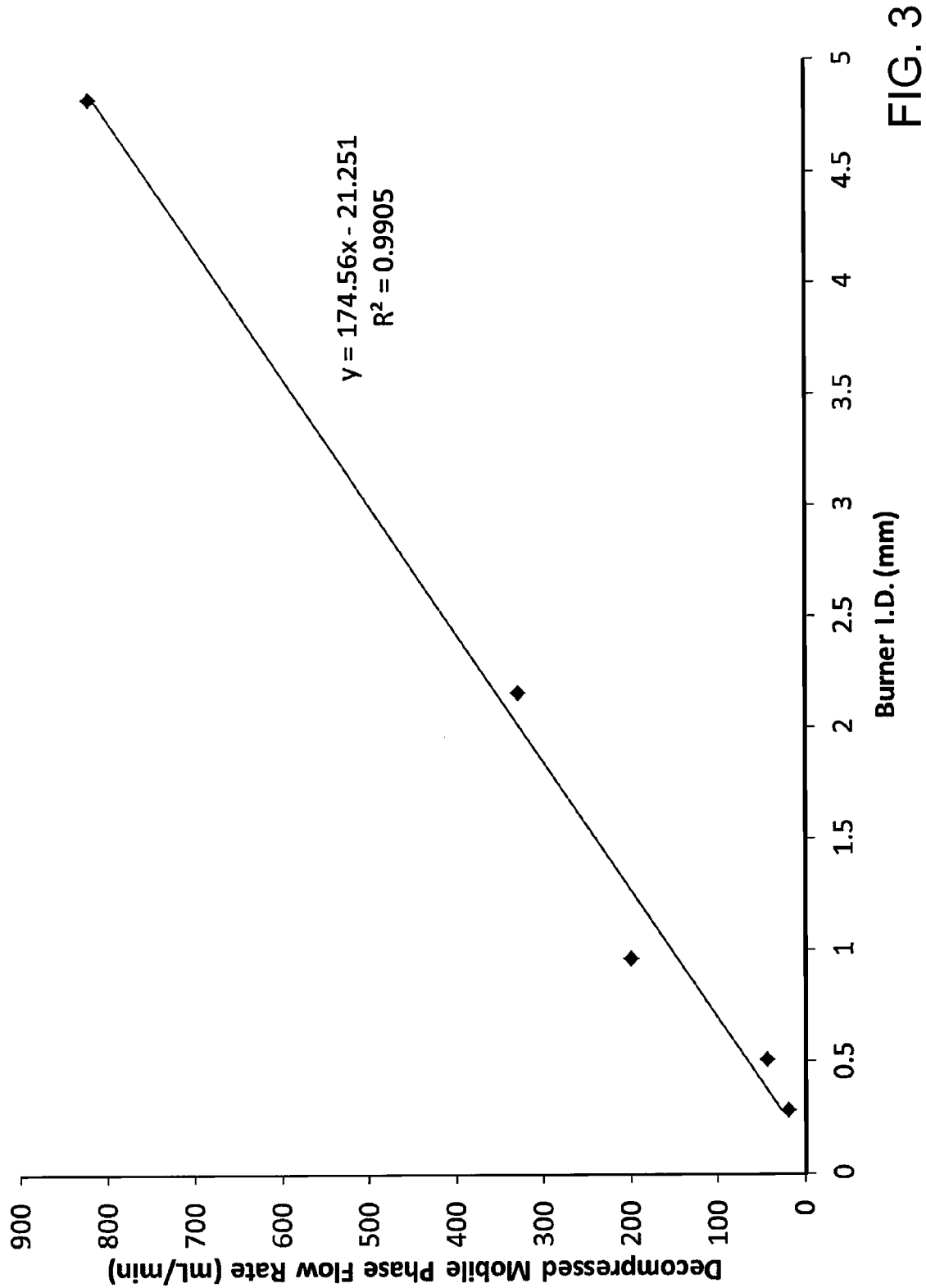
FIG. 3 shows a least-squares linear regression plot of FID inner burner i.d. values versus mobile phase flow rates.

FIG. 3 shows a least-squares linear regression plot for the data above. The mobile phase flow rates determined above were plotted against the corresponding burner inner diameters. Plotting and linear regression were performed in MS Excel.

While this disclosure has been particularly shown and described with reference to example embodiments thereof, it will be understood by those skilled in the art that various changes in form and details may be made therein without departing from the scope of the invention encompassed by the appended claims.

What is claimed is:

1. A method of matching a chromatographic column with a FID inner burner, comprising:
   (i) providing a chromatographic column with an internal diameter;
   (ii) determining an optimal mobile phase flow rate for the chromatographic column;
   (iii) calculating an optimal inner diameter of the inner burner that combined with the internal diameter and flow rate of the column produces optimal detector performance, by calculating the optimal inner diameter of the FID inner burner according to:

$d = \mu/175$ wherein d is the optimal inner diameter of the FID inner burner in mm, $\mu$ is a decompressed optimal mobile phase flow rate in mL/min, and constant 175 has units of mL/(min·mm); and
   (iv) providing a FID inner burner having an inner diameter substantially equal to the calculated optimal inner diameter.

2. The method of claim 1, wherein providing the FID inner burner comprises selecting a commercially available FID inner burner having an inner diameter within +/−50% of the calculated optimal inner diameter.

3. The method of claim 1, wherein the step of determining an optimal mobile phase flow rate comprises determining the flow rate which has the lowest minimum plate height as determined by the van Deemter Equation for the chromatographic column.

4. The method of claim 1, wherein the mobile phase comprises carbon dioxide.

5. The method of claim 1, wherein the mobile phase comprises a material selected from the group consisting of helium, nitrogen, and combinations thereof.

6. The method of claim 1, wherein the internal diameter of the chromatographic column is between about 0.05 mm and about 50.0 mm.

7. The method of claim 1, wherein the inner diameter of the FID inner burner is between about 0.1 mm and about 13.0 mm.

8. The method of claim 1, further comprising installing the FID inner burner within a fixed FID outer burner.

9. A method of matching a chromatographic column with a FID inner burner, comprising:
   (i) providing a chromatographic column with an internal diameter;
   (ii) experimentally determining a maximum stable decompressed mobile phase flow rate for each of a plurality of different FID inner burner inner diameters;
   (iii) determining a constant k which is the slope of a linear regression plot formed by plotting the maximum stable decompressed mobile phase flow rates against the corresponding FID inner burner inner diameters;
   (iv) determining an optimal mobile phase flow rate for the chromatographic column;
   (v) calculating an optimal inner diameter of the inner burner that combined with the internal diameter and flow rate of the column produces optimal detector performance by determining an optimal inner burner inner diameter according to the equation $d = \mu/k,$ wherein d is the optimal inner burner inner diameter, k is the constant k, and $\mu$ is a decompressed optimal mobile phase flow rate; and
   (vi) providing a FID inner burner having an inner diameter substantially equal to the calculated optimal inner diameter.

* * * * *